United States Patent [19]

Barnes

[11] Patent Number: 5,496,324
[45] Date of Patent: Mar. 5, 1996

[54] PROXIMAL BODY MILLING APPARATUS

[75] Inventor: Milton F. Barnes, Warsaw, Ind.

[73] Assignee: Zimmer, Inc., Warsaw, Ind.

[21] Appl. No.: 262,711

[22] Filed: Jun. 20, 1994

[51] Int. Cl.$^6$ .......................... A61B 17/16; A61B 17/17
[52] U.S. Cl. ..................... 606/79; 409/179; 409/201; 82/1.5; 606/89
[58] Field of Search ................. 606/79, 80, 86, 606/87, 89; 409/200, 178, 179; 409/201, 175; 82/1.2, 1.5, 1.3, 1.4

[56] References Cited

U.S. PATENT DOCUMENTS

| | | | |
|---|---|---|---|
| 5,342,366 | 8/1984 | Whiteside et al. | 606/86 |
| 5,417,695 | 5/1995 | Axelson, Jr. | 606/89 |

Primary Examiner—Tamara L. Graysay
Attorney, Agent, or Firm—Todd A. Dawson

[57] ABSTRACT

A milling apparatus 2 including an articulated cutter 20 and an inverted L-shaped frame 10 for removing a unique geometric volume of bone to receive a prosthetic implant stem. Cutter 20 is housed within frame 10 for rotational movement about its longitudinal axis and lateral movement along a guide 16, which extends laterally from frame 10. Cutter 20 includes a pair of articulated arms 30, 32 each carrying a plurality of cutting blades 40. The proximal end 22 of cutter 20 is seated in an elongated non-radial race 17 formed in guide 16. Articulated arms 30, 32 provide a "scissoring" action which allows cutter 20 to be compressed longitudinally when shifted to one end of race 17 and extended longitudinally when shifted to the opposite end of race 17. The scissoring action of arms 30, 32 also changes the angle of the cutting face of blades 40 carried by arms 30, 32. Consequently, milling apparatus 2 creates a receiving cavity having an egg-shaped cross section.

3 Claims, 8 Drawing Sheets

PROXIMAL BODY MILLING APPARATUS

This invention relates to an apparatus for preparing a cavity to receive a prosthetic implant and has specific relevance to a milling apparatus for preparing a cavity with an egg-shaped cross section.

BACKGROUND OF INVENTION

In hip replacement procedures, a cavity must be formed in the medullary channel to receive a femoral implant stem. Implant stems generally have an egg-shaped cross section similar to the cross section of the femur. The receiving cavity must conform to the geometry of the implant stem. Milling the bone stock to form the cavity is preferable to reduce the trauma to the bone tissue.

A variety of broaches, rasps and milling instruments have been developed to prepare a cavity for receiving an irregularly shaped implant stem. Milling devices such as the ones described in U.S. Pat. No. 5,047,033 are used to cut and shape the cavities for custom fitted implants. The milling device includes a V-shaped guide frame having a lower end base portion that is adapted to extending into the medullary channel, and a pair of spaced struts. The lower end has one or more receptacles for holding the end of the mill or rotary reamer. This apparatus can be used to produce an irregular cavity but the anterior and posterior volumes of an egg-shaped cavity are not created simultaneously.

SUMMARY OF INVENTION

The milling instrument of this invention uses an articulated cutter and an inverted L-shaped frame to prepare a cavity with an egg-shaped cross section. The frame includes an upright neck and a laterally extending guide. The cutter is housed within the frame for rotational movement about its longitudinal axis and lateral movement along the guide. The cutter includes a globular head and a distal end hingably connected by a pair of articulated arms. The articulated arms include an upper part and a lower part, which are hinged together. The lower part of each articulated arm carries a plurality of cutting edges or blades which shave the bone stock as the cutting assembly is rotated. The distal end of the cutter is seated within a bearing, which is pivotally connected to the distal end of the upright neck. The globular head is shiftably seated within an elongated non-radial race formed in the guide. Since the race is non-radial, the length of the cutter measured along its longitudinal axis changes as the cutter moves back and forth along the cutter race. The articulated arms provide a scissoring action which allows the cutter to be compressed longitudinally when shifted to one end of the race and extended longitudinally when shifted to the opposite end of the race. The scissoring action of the articulated arms also changes the angle of the blade's cutting face carried by the lower arm parts. The rotating cutter removes more bone stock when the cutter is compressed by being shifted to one end of the race than when the cutter is extended by being shifted to the opposite end of the race. Consequently, the milling instrument creates a receiving cavity having an egg-shaped cross section.

Accordingly, an advantage of this invention is to provide for a milling instrument for removing a unique volume of bone stock which includes a cutting member that rotates about a non-stationary axis.

Another advantage is to provide a milling apparatus for cutting a cavity in a bone with an egg-shaped cross section for receiving an implant stem.

Another advantage is to provide for a milling apparatus for simultaneously cutting an anterior and posterior volume of a cavity with an egg-shaped cross section.

Other advantages will become apparent upon a reading of the following description.

BRIEF DESCRIPTION OF THE DRAWINGS

A preferred embodiment of the invention has been depicted for illustrative purposes only wherein.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

Figure 5:
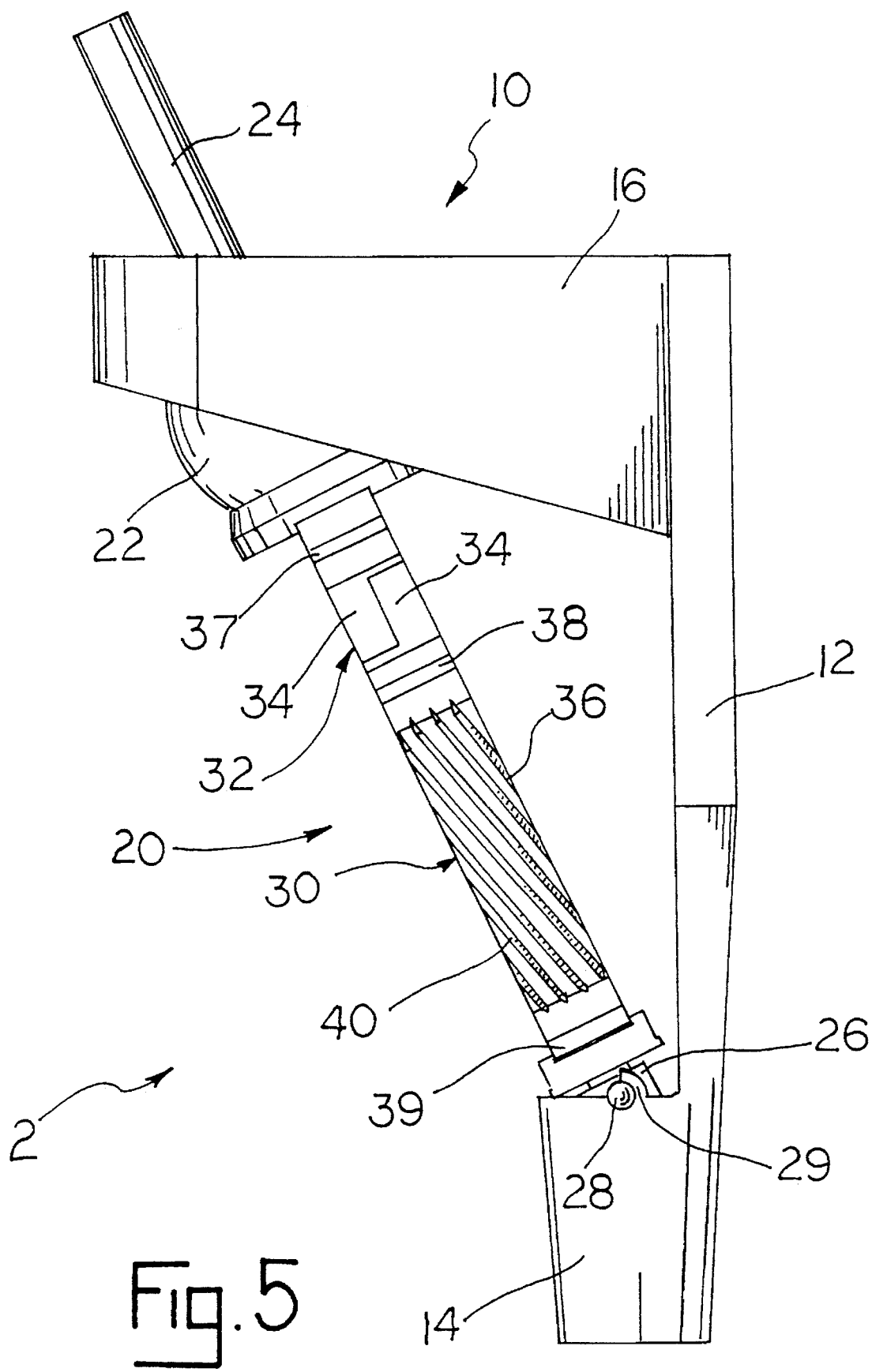
FIG. 5 is a side view of the milling instrument showing the cutter fully extended and pivoted to the outer most end of the cutter race.
Figure 6:
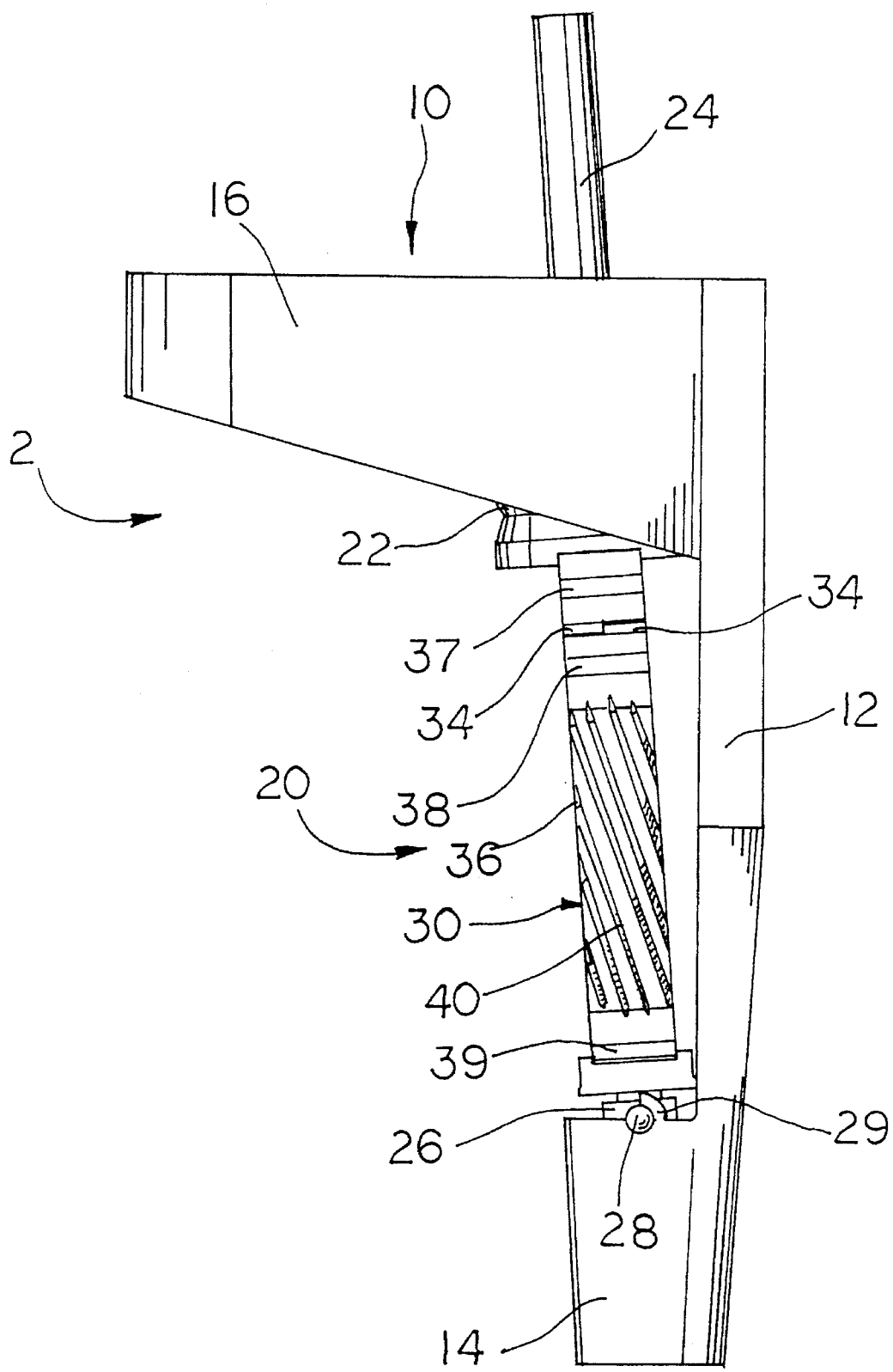
FIG. 6 is a side view of the milling instrument showing the cutter fully compressed and pivoted to the inner most end of the cutter race.
Figure 7:
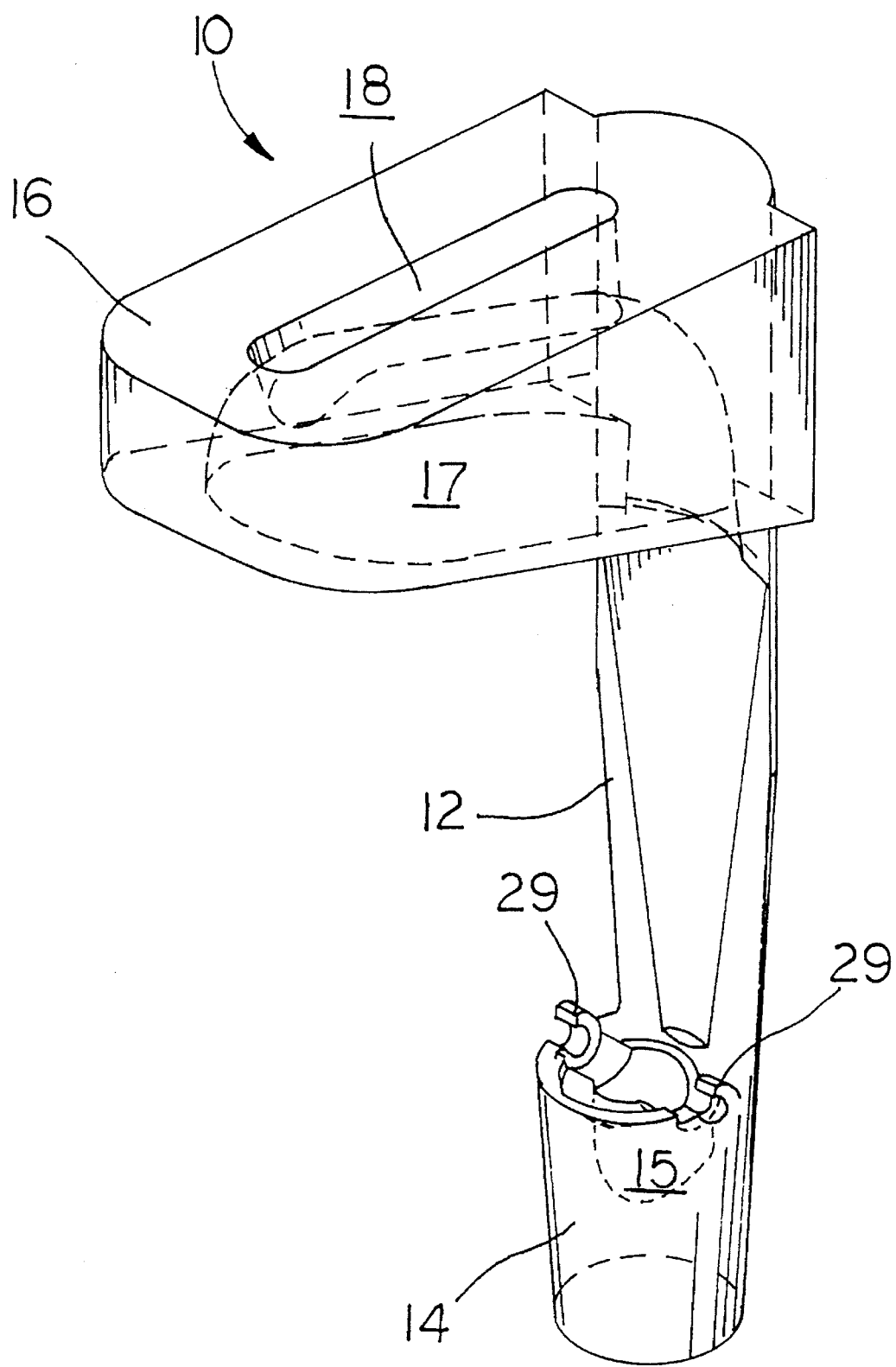
FIG. 7 is a perspective view of the frame.

The milling apparatus 2 of this invention is preferably made of stainless steel, although any suitable material may be used. Milling apparatus 2 includes an articulated and rotatable cutter 20 and an inverted L-shaped frame 10. As best shown in FIG. 7, frame 10 includes a neck 12 which forms the upright leg of the frame and a cutter guide 16 which forms the horizontal leg of the inverted L-shaped frame. The distal end of neck 12 includes a head 14, which is configured to be driven into the medullary channel of the femur. Frame head 14 has a bearing cavity 15 for receiving the distal end of cutter 20. In addition, frame head 14 may be adapted for attachment with an alignment post (not shown), which is used to axially align and rotationally orient milling apparatus 2. As shown in FIGS. 5-7, guide 16 extends from the upper end of neck 12 at an obtuse angle to neck 12 and has a longitudinal cutter race 17 formed in its lower face. As shown in FIG. 7, cutter race 17 is non-radial, meaning that the distance between frame head 14 and the outermost lateral end of race 17 is greater than the distance between the frame head and the innermost lateral end of the race. A longitudinal slot 18 extends through the upper face of guide 16 into race 17.

Figure 9:
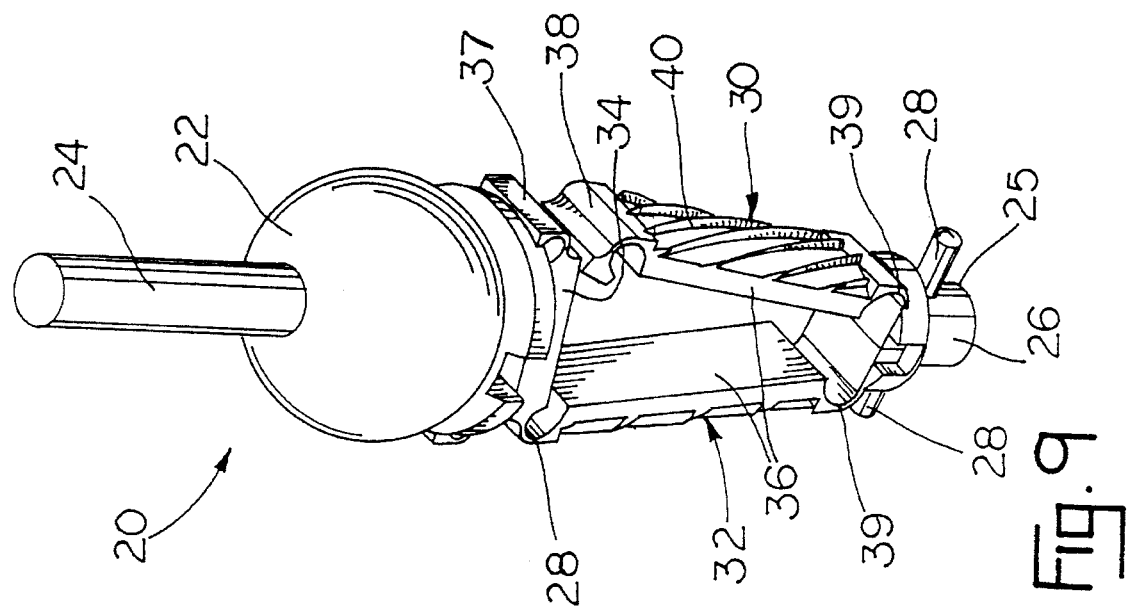
FIG. 9 is a perspective view of the cutter in a compressed position.
Figure 8:
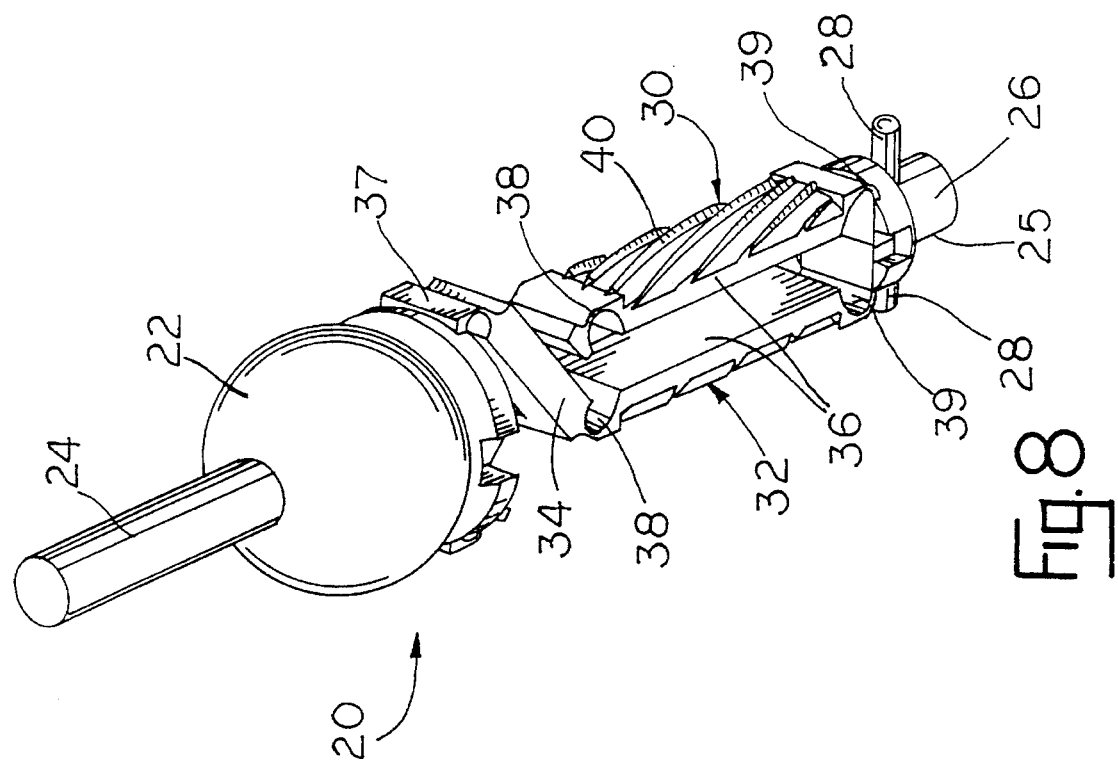
FIG. 8 is a perspective view of the cutter in an extended position.

As best shown in FIGS. 8 and 9, cutter 20 includes a shiftable globular end or head 22, and a fixed distal end 25, and a pair of articulated arms 30, 32. A drive shaft 24 extends axially from cutter head 22. Shaft 24 is adapted for connection to a torque device for rotating the cutter. Distal end 25 of cutter 20 is seated within a bearing 26. Bearing 26 facilitates rotational movement of cutter 20 about its longitudinal axis (axis of rotation). As shown in FIGS. 1-6, bearing 26 is pivotally connected to frame head 14. Bearing 26 is seated within bearing cavity 15 of frame head 14 and secured by pivot pins 28 which are journaled by tabs 29. Cutter head 22 is shiftably seated within cutter race 17 and shaft 24 extends through slot 18 into guide 12. Articulated arms 30, 32 are hingably connected between cutter head 22 and distal end 25. Each arm 30, 32 includes an upper part 34 and a lower part 36. A plurality of cutting blades 40 are formed on the outer face of each lower arm part 36. Each upper arm part 34 is connected to its lower arm part 36 by a flexible integral joint 38. Joints 38 are formed by areas of thinned junctures which allow flexible bending thereby producing a resilient joint. The proximal end of each upper arm part 34 is hingably connected by a similar integral joint 37. The distal end of each lower arm part 36 is pivotally connected to bearing 26 by integral joint 39. Joints 39 are similar to joints 38 and 37. Although the preferred embodiment shown herein uses integral joints to hingably connect the integral arms, other types of conventional hinges may be employed. The tension from joints 37, 38 and 39 ensures that cutter head 22 remains seated within race 17.

As shown in FIGS. 1-6, cutter 20 can be freely rotated about its longitudinal axis. In addition, cutter 20 can be shifted radially about an axis through pins 28, which are perpendicular to the cutter's longitudinal axis. Cutter head 22 moves laterally along the length of cutter race 17. Since race 17 is non-radial, the length of the cutter measured along its longitudinal axis changes as the cutter moves back and forth along the race. Articulated arms 30, 32 provide a scissoring action which allows cutter 20 to be compressed and expanded longitudinally. The scissoring action of articulated arms 30, 32 determines the angle of the cutting face carried by lower arm parts 36.

Figure 1:
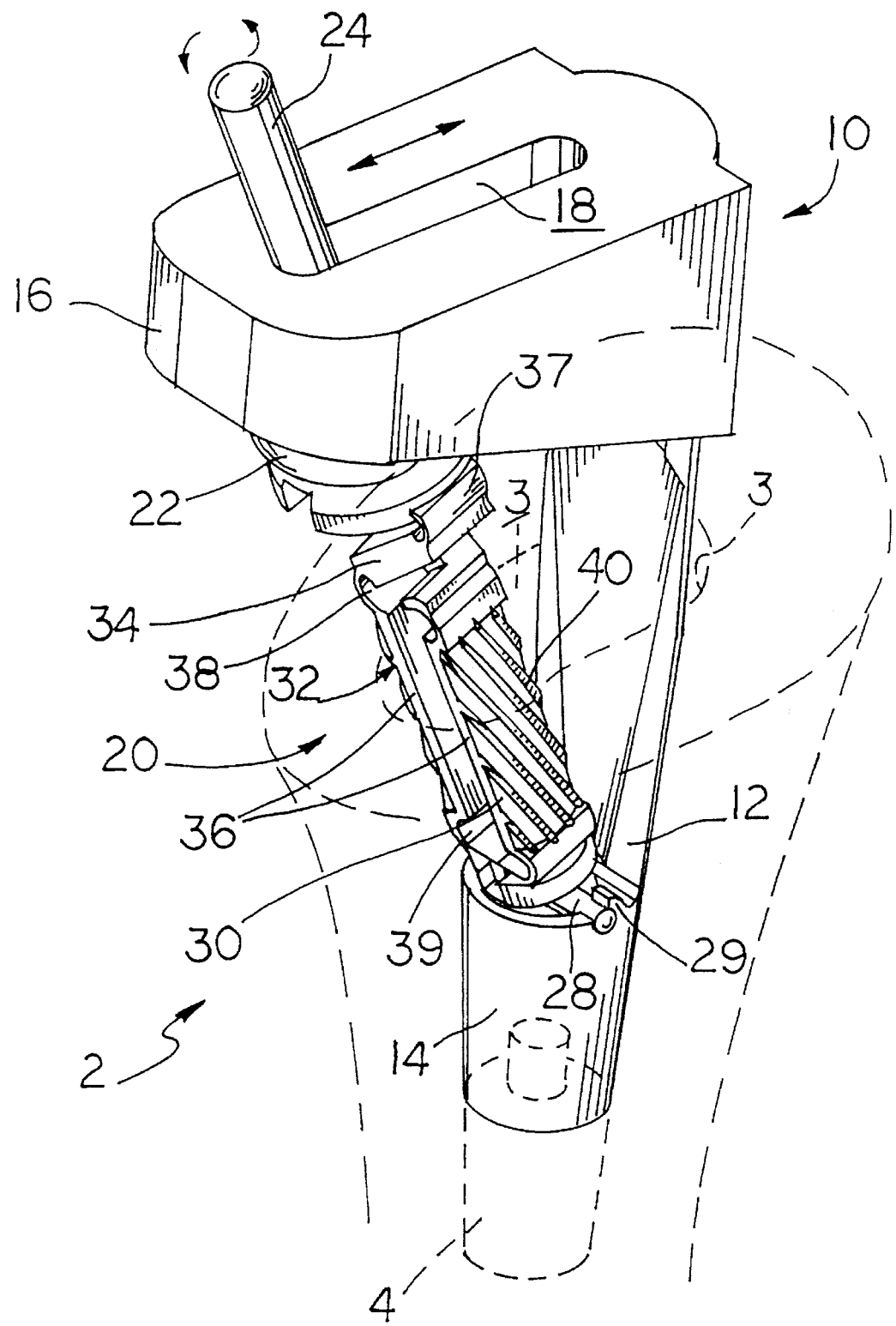
FIG. 1 is a perspective view of the milling instrument showing the cutter fully extended and pivoted to its outer most end of the cutter race.
Figure 2:
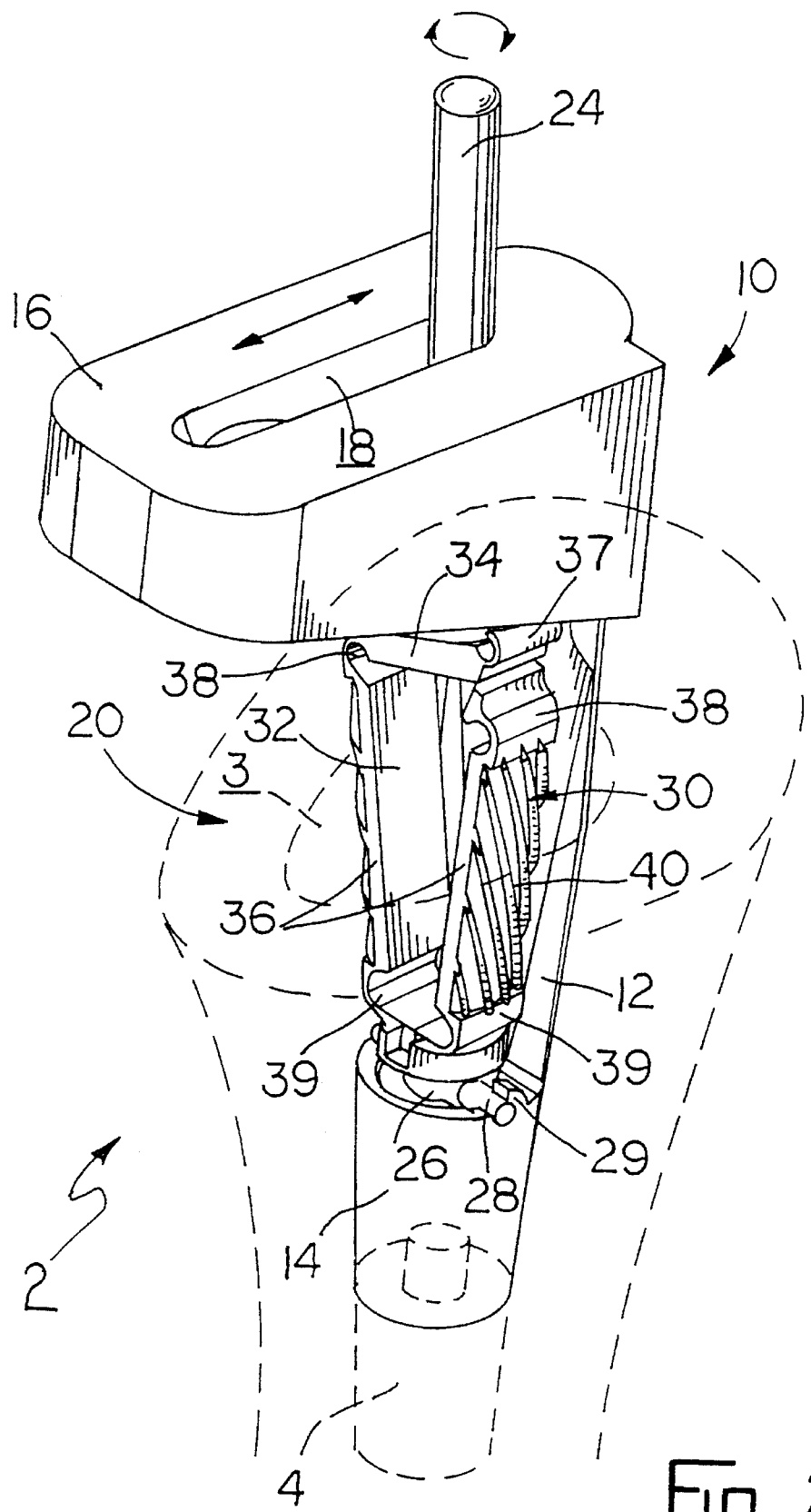
FIG. 2 is a perspective view of the milling instrument showing the cutter fully compressed and pivoted to its inner most end of the cutter race.
Figure 3:
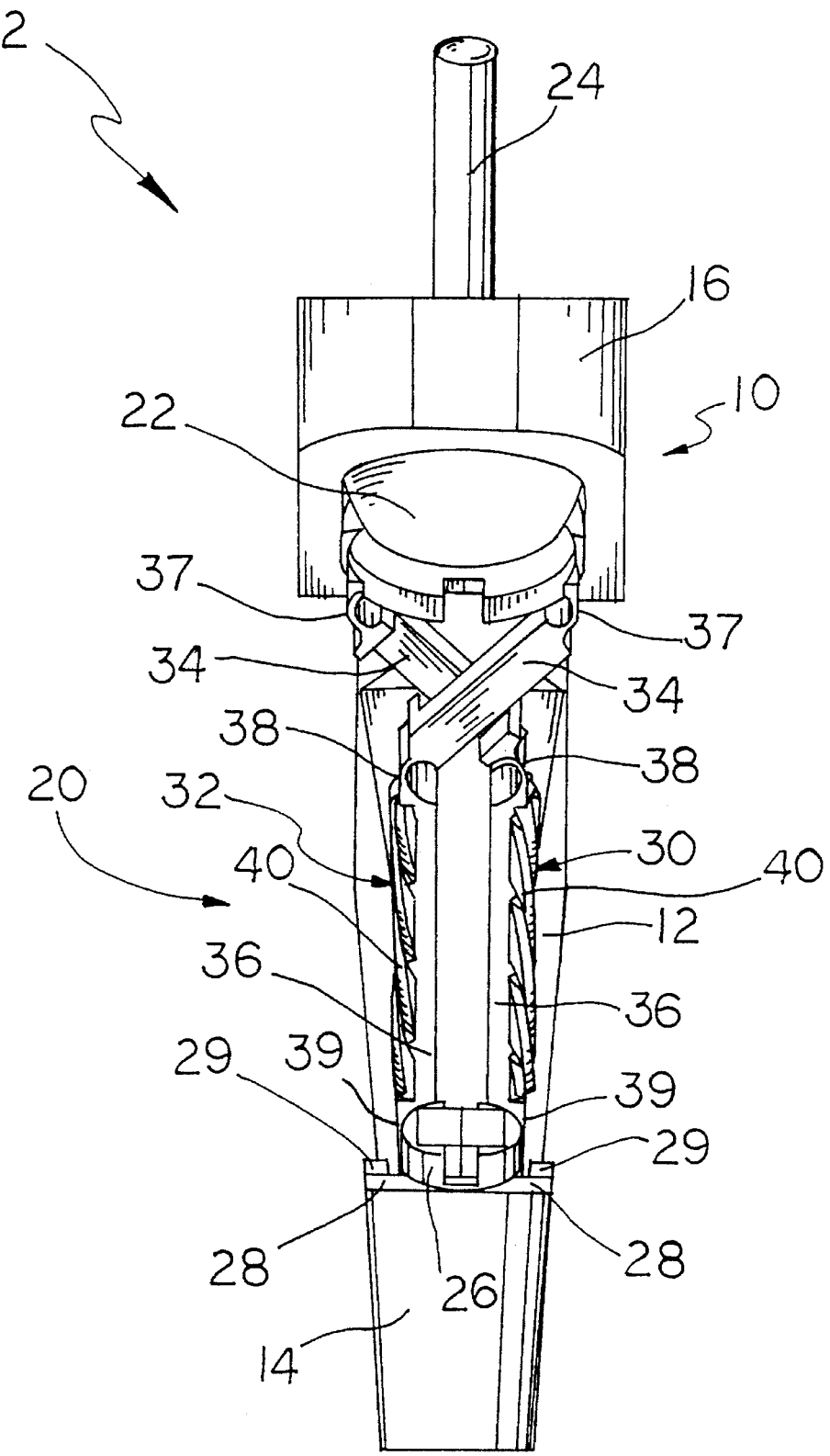
FIG. 3 is a front view of the milling instrument showing the cutter fully extended and pivoted to the outer most end of the cutter race.
Figure 4:
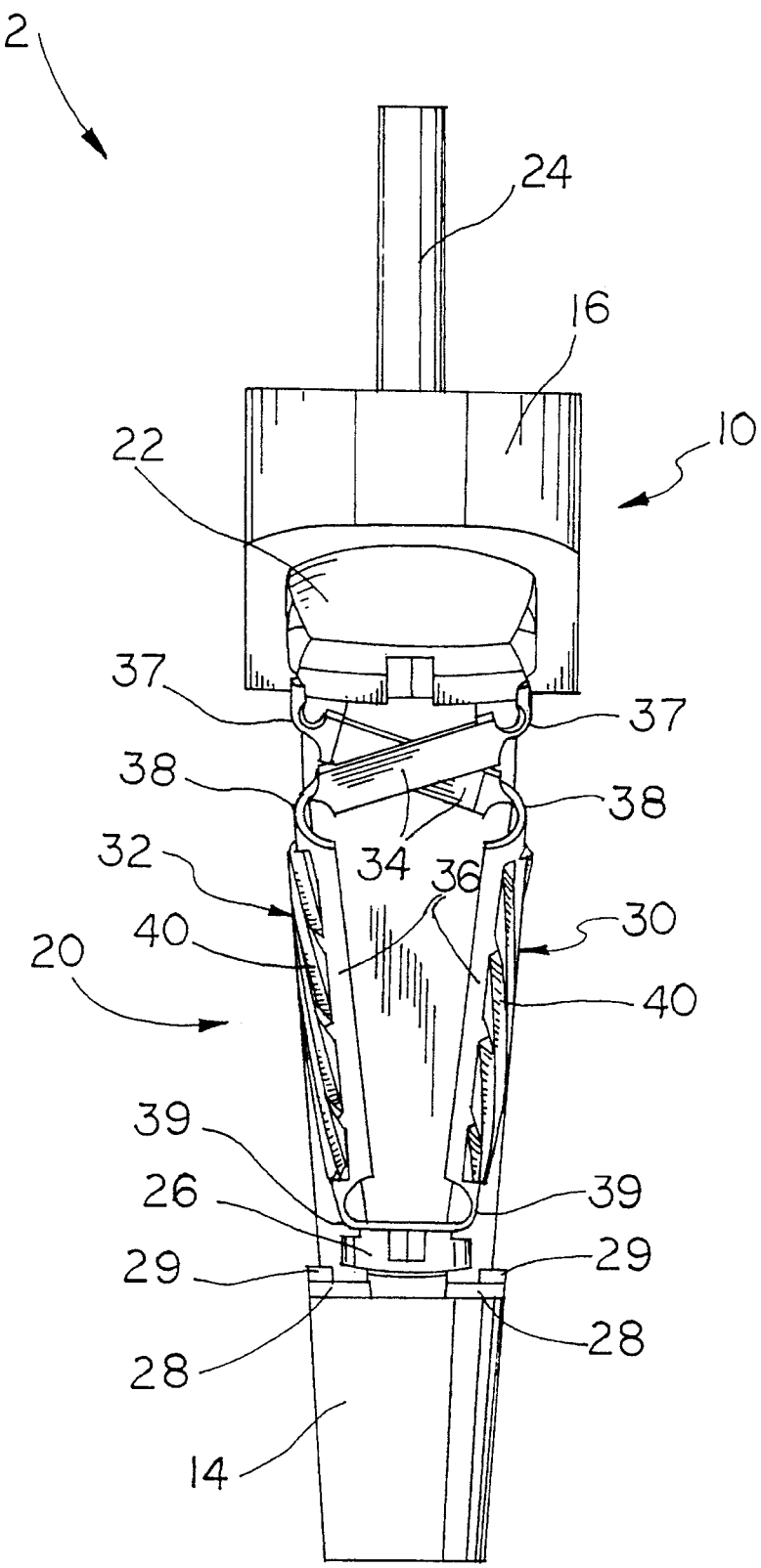
FIG. 4 is a front view of the milling instrument showing the cutter fully compressed and pivoted to the inner most end of the cutter race.

FIGS. 1, 3 and 5 show cutter 20 shifted to the outer most lateral end of race 17 and fully extended. As shown, upper arm part 34 and lower arm part 36 are substantially parallel to the cutter's longitudinal axis (axis of rotation). Consequently, the angle of the cutting face of blades 40 is substantially parallel with the axis of rotation. FIGS. 2, 4 and 6 show cutter 20 shifted to the inner most lateral end of race 17 and fully compressed. As cutter 20 is compressed by its lateral movement toward the inner most lateral end of race 17, the distal ends of upper arm parts 34 pivot outward forcing the proximal ends of lower arm parts 36 outward away from the cutter's axis of rotation. The outward displacement of articulated arms 30, 32 increases the angle of the cutting face of blades 40 carried on lower arm parts 36. Increasing the angle of the cutting face of blades 40, allows more bone stock to be removed as the cutter is rotated.

For illustration purposes only, the operation of milling apparatus 2 will be described for use in a revisionary hip implant replacement, although the apparatus can be adapted for use in the original implant procedure. After the original implant stem (not shown) is removed and the initial cavity 3 is cleared of debris, milling apparatus 2 is inserted into initial cavity 3 with guide 16 overlying the proximal end of the femur. An alignment post 4 may be used to properly position and seat the milling apparatus within the initial cavity. Once milling apparatus 2 is seated and oriented in initial cavity 3, a torque drive device (not shown) is connected to shaft 24. The torque drive device rotates cutter 20 inside frame 10. Rotation of cutter 20 shaves portions of the bone stock from the cavity. The surgeon guides the rotating cutter back and forth along the length of slot 18. The resulting cavity has an egg-shaped cross section with a greater volume being removed when the cutter is shifted to the inner most extremity.

The milling instrument of this invention shows cutter head 22 uni-laterally shiftable within cutter race 17; however, the race and guide can be formed to allow for multilateral movement of the cutter head within the guide to remove a unique geometric volume of bone. Furthermore, while the preceding exemplary embodiments have focused on a milling apparatus used in a femoral implantation procedure, it will be understood that the apparatus and techniques described are applicable to other types of implantation procedures, the geometry of the apparatus being adjusted accordingly. Likewise, it is understood that the above description does not limit the invention to the details given, but may be modified within the scope of the following claims.

I claim:

1. An apparatus used to cut a cavity in a bone for receiving an implant comprising:

a frame part having a distal end insertable into said bone, a guide extending laterally from said frame and having a race defined therein, said race having a first end and a second end, an articulated cutter having a longitudinal axis and being pivotally connected to said frame and carded within said guide for rotation about the cutter's longitudinal axis and for movement within said race, said articulated cutter including a first arm part, a second arm part and a shaft, the second arm part includes blade means for removing a portion of said bone when said cutter is rotated, the first arm part is hingeably connected to the shaft at one end and to the second arm part at an opposite end, said shaft defining the longitudinal axis of the articulated cutter, said articulated cutter being responsive to contact with said race for positioning said second arm part and the blade substantially parallel to said cutter's longitudinal axis when said cutter is shifted to the first end of said race and for angularly positioning said second arm part and the blade away from said cutter's longitudinal axis when said cutter is shifted toward its second end.

2. The apparatus of claim 1 wherein the linear distance between said frame distal end and said race first end is substantially different than the distance between said frame distal end and said race second end.

3. The apparatus of claim 1 wherein said cutter includes beating means at its distal end adjacent the pivotal connection between the articulated cutter and the frame for accommodating rotational movement of said cutter about its said longitudinal axis.

* * * * *